(12) United States Patent
Yamaguchi et al.

(10) Patent No.: US 6,528,672 B2
(45) Date of Patent: Mar. 4, 2003

(54) PERFLUOROPOLYETHER-MODIFIED AMINOSILANE, SURFACE TREATING AGENT AND COATED ARTICLE

(75) Inventors: Hiromasa Yamaguchi, Gunma-ken (JP); Koichi Yamaguchi, Gunma-ken (JP); Hirofumi Kishita, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/977,314

(22) Filed: Oct. 16, 2001

(65) Prior Publication Data

US 2002/0071959 A1 Jun. 13, 2002

(30) Foreign Application Priority Data

Oct. 16, 2000 (JP) ........................................ 2000-314657

(51) Int. Cl.⁷ .............................. C07F 7/10; C08L 83/05
(52) U.S. Cl. .................. 556/419; 556/420; 406/287.11; 406/287.14; 406/287.16; 428/429; 428/447; 428/450; 428/451
(58) Field of Search ................................. 556/419, 420; 106/287.11, 287.14, 287.16; 428/429, 447, 450, 451

(56) References Cited

U.S. PATENT DOCUMENTS 5,705,591 A * 1/1998 Matsuda et al. ........ 556/419 X
6,200,684 B1   3/2001 Yamaguchi et al.

FOREIGN PATENT DOCUMENTS

| JP | 58-167597 | 3/1983 |
| JP | 58-122979 | 7/1983 |
| JP | 11-29585  | 2/1999 |

* cited by examiner

Primary Examiner—Paul F. Shaver
(74) Attorney, Agent, or Firm—Birch, Stewart, Kolasch & Birch, LLP

(57) ABSTRACT

A novel perfluoropolyether-modified aminosilane cures into a film having improved water and oil repellency and anti-staining properties. A surface treating agent comprising the aminosilane, and an article with a coating of the aminosilane are also provided.

6 Claims, 1 Drawing Sheet

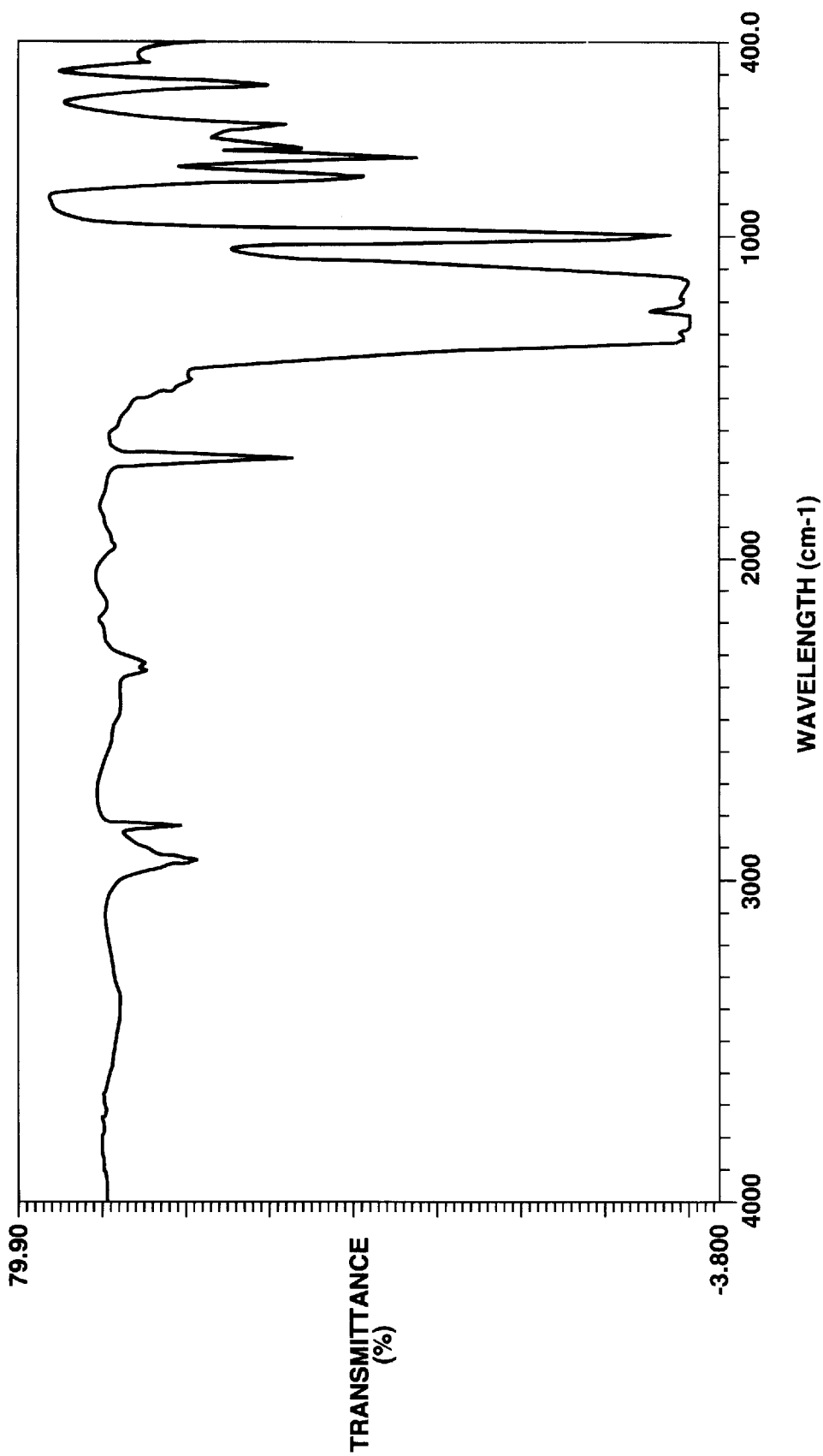

PERFLUOROPOLYETHER-MODIFIED AMINOSILANE, SURFACE TREATING AGENT AND COATED ARTICLE

This invention relates to novel perfluoropolyether-modified aminosilanes capable of forming cured coatings having water repellency, oil repellency, parting and anti-staining properties, durability and lubricity, surface treating agents comprising the same, and articles having cured coatings of the aminosilanes.

BACKGROUND OF THE INVENTION

In general, perfluoropolyether-containing compounds have water and oil repellency, chemical resistance, lubricity, parting and anti-staining properties because of their very low surface energy. For the effective utilization of such properties, these compounds are widely used in the industry as water/oil repellent anti-staining agents for paper and fibers, lubricants in magnetic recording media, oil repellants in precision machines, parting agents, cosmetic ingredients, and protective coatings.

The same properties, however, suggest that perfluoropolyether-containing compounds are non-tacky and non-adherent to other substrates. They are applicable to the substrate surface, but cannot form a coating firmly bonded to the substrate.

Silane coupling agents are well known as the means for establishing a firm bond between a substrate surface such as glass or fabric and an organic compound. The silane coupling agent has an organic functional radical and a reactive silyl radical (typically alkoxysilyl radical) in a molecule. The alkoxysilyl radical undergoes self-condensation reaction with air-borne moisture, converting to a siloxane to form a coating. At the same time, the silane coupling agent forms chemical and physical bonds with the surface of glass or metal, resulting in a durable tough coating. By virtue of these advantages, the silane coupling agent is widely used as a coating agent to a variety of substrates.

As one exemplary compound which exhibits the above-mentioned characteristics, JP-A 58-167597 discloses fluoroaminosilane compounds of the following formula (2):

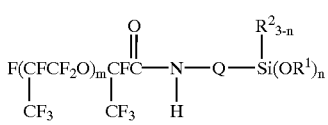

wherein $R^1$ and $R^2$ each are an alkyl radical of 1 to 4 carbon atoms, Q is $CH_2CH_2CH_2$ or $CH_2CH_2NHCH_2CH_2CH_2$, m is an integer of 1 to 4, and n is 2 or 3. These compounds, however, fail to fully take advantage of the perfluoropolyether radical because the perfluoropolyether radical portion is as short as consisting of two to five monomer units of hexafluoropropylene oxide (HFPO).

Also, JP-A 58-122979 discloses compounds of the following formula (3) as a water and oil repellant to be applied to glass surface.

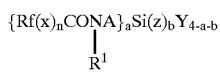

Herein, Rf is a polyfluoroalkyl radical having 1 to 20 carbon atoms, which may contain at least one ether bond, $R^1$ is hydrogen or lower alkyl, A is alkylene, x is —$CON(R^2)$—Q— or —$SO_2N(R^2)$—Q— wherein $R^2$ is lower alkyl and Q is a divalent organic radical, z is lower alkyl, Y is halogen, alkoxy or $R^3COO$— wherein $R^3$ is hydrogen or lower alkyl, n is 0 or 1, a is 1, 2 or 3, and b is 0, 1 or 2. These compounds do not exert fully satisfactory effects because the number of carbon atoms in the fluorinated radical portion is as small as 1 to 20 carbon atoms.

To solve the above-discussed issues, the inventors proposed in JP-A 11-29585 perfluoropolyether-modified aminosilanes of the following formula (4).

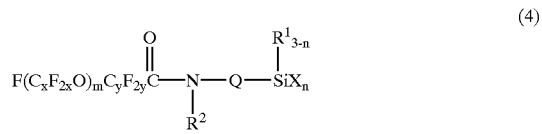

Herein X is a hydrolyzable radical, $R^1$ is lower alkyl, $R^2$ is hydrogen or lower alkyl, Q is $CH_2CH_2CH_2$ or $CH_2CH_2NHCH_2CH_2CH_2$, m is an integer of 6 to 50, n is 2 or 3, x and y each are an integer of 1 to 3. These perfluoropolyether-modified aminosilanes have improved water repellency, oil repellency, anti-staining, chemical resistance, lubricity, parting and other properties, and can be utilized as a surface treating agent which is applied to the surface of various substrates. However, curing takes a long time because of a lower proportion (in wt %) of hydrolyzable radicals per molecule. Some improvements in film formation were desirable.

To overcome the above drawback, the inventors further proposed in Japanese Patent Application No. 11-139596 perfluoropolyether-modified aminosilanes of the following formula (5).

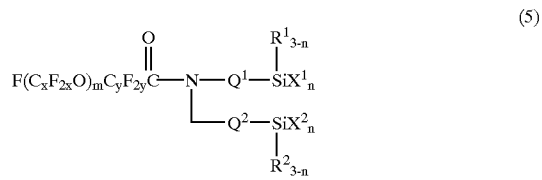

Herein $X^1$ and $X^2$ each are a hydrolyzable radical, $R^1$ and $R^2$ each are lower alkyl or phenyl, $Q^1$ and $Q^2$ each are a divalent organic radical, m is an integer of 6 to 50, n is 2 or 3, x and y each are an integer of 1 to 3. It would be desirable to improve the durability and lubricity of these aminosilanes.

Since many tall buildings are constructed in the recent decades, the demand for the technology for imparting "stain resistance" or "ease of stain removal" for keeping glazing maintenance-free is increasing. The same technology is also required in order that display screens be fingerprint-free for better outer appearance and visibility. There is a desire to have a material meeting such demands.

SUMMARY OF THE INVENTION

An object of the invention is to provide a perfluoropolyether-modified aminosilane capable of forming a cured coating which firmly bonds to substrates and has improved lubricity and durability. Another object is to provide a surface treating agent comprising the aminosilane and an article having a cured coating of the aminosilane formed thereon.

We have found that a novel perfluoropolyether-modified aminosilane of the following general formula (1) is improved in water repellency, oil repellency, chemical resistance, durability, lubricity, anti-staining and parting properties, can be used as a surface treating agent by applying to the surface of various substrates. A cured coating of the aminosilane is in firm bond to the substrate so that it may sustain the effects over a long period of time.

The present invention provides a perfluoropolyether-modified aminosilane having the formula (1):

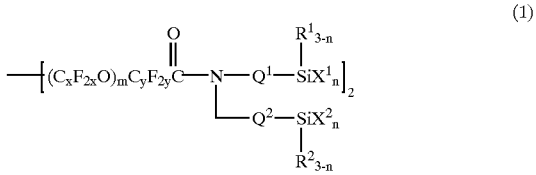

wherein $X^1$ and $X^2$ each are a hydrolyzable radical, $R^1$ and $R^2$ each are a lower alkyl radical or phenyl radical, $Q^1$ and $Q^2$ each are a divalent organic radical, m is an integer of 2 to 50, n is 2 or 3, x is an integer of 1 to 4, and y is an integer of 0 to 4.

The invention also provides a surface treating agent primarily comprising the aminosilane and/or a partial hydrolytic condensate thereof, and an article of manufacture having on its surface a cured coating primarily comprising the aminosilane and/or a partial hydrolytic condensate thereof.

The perfluoropolyether-modified aminosilane of formula (1) serving as a main component of the surface treating agent contains amide linkages. Amide linkages are known effective for efficient orientation of modifying fluoride radicals to the substrate surface. In this regard too, the surface treating agent of the invention is superior to conventional ones. Additionally, the aminosilane of the invention has two hydrolyzable silyl radicals at each end of the molecule so that the ends are firmly bound to the substrate, leading to improvements in lubricity and durability.

BRIEF DESCRIPTION OF THE DRAWING

The only FIGURE, FIG. 1 shows an IR spectrum of the compound synthesized in Synthesis Example 1.

DESCRIPTION OF THE PREFERRED EMBODIMENTS

The perfluoropolyether-modified aminosilane of the invention has the formula (1).

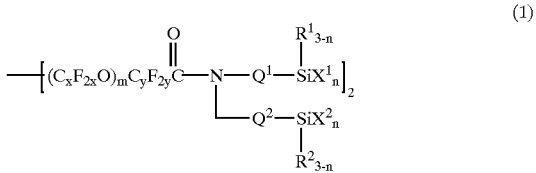

Herein $X^1$ and $X^2$ each are a hydrolyzable radical, $R^1$ and $R^2$ each are a lower alkyl radical or phenyl radical, $Q^1$ and $Q^2$ each are a divalent organic radical, m is an integer of 2 to 50, n is 2 or 3, x is an integer of 1 to 4, and y is an integer of 0 to 4.

More particularly, $X^1$ and $X^2$ stand for hydrolyzable radicals and may be the same or different. Illustrative examples include alkoxy radicals of 1 to 10 carbon atoms such as methoxy, ethoxy, propoxy and butoxy, oxyalkoxy radicals of 2 to 10 carbon atoms such as methoxymethoxy and methoxyethoxy, acyloxy radicals of 1 to 10 carbon atoms such as acetoxy, alkenyloxy radicals of 2 to 10 carbon atoms such as isopropenoxy, and halogen radicals such as chloro, bromo and iodo. Of these, methoxy, ethoxy, isopropenoxy and chloro are preferred.

$R^1$ and $R^2$ stand for lower alkyl radicals of 1 to 5 carbon atoms or phenyl radicals and may be the same or different. Exemplary radicals include methyl, ethyl and phenyl, with methyl being most preferred.

$Q^1$ and $Q^2$ stand for divalent organic radicals and may be the same or different. Among others, alkylene radicals of 1 to 10 carbon atoms such as $CH_2CH_2CH_2$ are preferred.

The letter m is an integer of 2 to 50. With m below the range, the characteristics of perfluoropolyether radical are not fully exerted. With m beyond the range, the proportion of alkoxysilyl radicals in the overall molecule becomes extremely low so that condensation reaction of alkoxysilyl radicals may be retarded, which is undesirable in forming a film. A value of m in the range of 10 to 30 is most desirable for a good balance between function development and reactivity. The letter n is either 2 or 3. A plurality of n's may be identical or different. A mixture of n=2 and n=3 may be used.

One exemplary process for preparing the perfluoropolyether-modified aminosilane of the invention is by hydrosilylation reaction of a diallylamide derivative of a corresponding hexafluoropropylene oxide (HFPO) oligomer with a corresponding hydroxysilane. For example, an aminosilane within the scope of the invention can be obtained by reacting a compound of formula (1a) with a compound of formula (1b) in the presence of a platinum group catalyst.

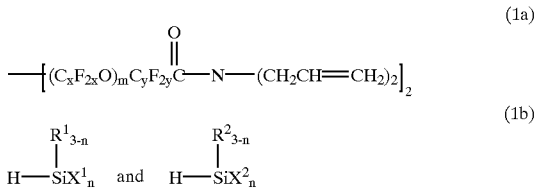

The present invention also provides a surface treating agent primarily comprising the perfluoropolyether-modified aminosilane defined above and/or a partial hydrolytic condensate thereof.

If necessary, a hydrolytic condensation catalyst may be added to the surface treating agent. Exemplary catalysts include organic tin compounds (e.g. dibutyltin dimethoxide and dibutyltin dilaurate), organic titanium compounds (e.g., tetra-n-butyl titanate), organic acids (e.g., acetic acid and methanesulfonic acid), and mineral acids (e.g., hydrochloric acid and sulfuric acid). Of these, acetic acid, tetra-n-butyl titanate and dibutyltin dilaurate are desirable. The catalyst is added in a catalytic amount, usually 0.01 to 5 parts by weight, especially 0.1 to 1 part by weight, per 100 parts by weight of the aminosilane and/or partial hydrolytic condensate thereof.

The surface treating agent of the invention may be diluted with a suitable solvent. Exemplary solvents include fluorine-modified aliphatic hydrocarbon solvents (e.g., perfluoroheptane and perfluorooctane), fluorine-modified aromatic hydrocarbon solvents (e.g., m-xylene hexafluoride and benzotrifluoride), fluorine-modified ether solvents (e.g., methylperfluorobutyl ether and perfluoro(2-butyltetrahydrofuran)), fluorine-modified alkylamine solvents (e.g., perfluorotributylamine and perfluorotripentylamine), hydrocarbon solvents (e.g., petroleum benzine, mineral spirits, toluene and xylene), and ketone solvents (e.g., acetone, methyl ethyl ketone and methyl isobutyl ketone). Of these, the fluorine-modified solvents are desirable from the standpoints of solubility and wettability. In particular, m-xylene hexafluoride, perfluoro (2-butyltetrahydrofuran) and perfluorotributylamine are desirable.

The solvents may be used alone or in admixture of any as long as the foregoing components are uniformly dissolved therein. The concentration of the aminosilane of formula (1) and/or partial hydrolytic condensate thereof in the solvent is preferably in the range of 0.01 to 50%, and especially 0.05 to 20% by weight although the optimum concentration depends on a particular treating technique.

The surface treating agent diluted with the solvent may be applied (differently stated, a substrate may be treated with the agent) by well-known techniques such as brush coating, dipping, spraying and evaporation. The optimum treating temperature varies with a particular treating technique, although a temperature from room temperature to about 120° C. is desirable when the agent is applied by brush coating or dipping. The application or treatment is desirably carried out under humidified conditions because humidity promotes the reaction. It is understood that appropriate treating conditions are selected on every application because the treating conditions vary depending on a particular silane compound and additives used.

The substrate to be treated with the surface treating agent is not critical. Various materials including paper, fabric, metals, metal oxides, glass, plastics, porcelain, and ceramics may be used as the substrate. More particularly, substrates of paper, fabric, metals, glass, plastics, ceramics, etc. are included when the surface treating agent is used as water and oil repellant; substrates for pressure-sensitive adhesive tape, resin molding molds, rolls, etc. are included when the surface treating agent is used as parting agent; and substrates of paper, fabric, metals, glass, plastics, ceramics, etc. are included when the surface treating agent is used as anti-staining agent.

The cured coating formed on the surface of substrates or articles generally has a thickness of 0.1 nm to 5 μm and especially 1 to 100 nm, although an appropriate thickness is selected depending on the type of substrate.

Illustrative applications of the surface treating agent include coatings for preventing fingerprint and grease contamination on optical members such as eyeglass lenses and anti-reflection filters; water repellent, anti-staining coatings on sanitary ware such as bathtubs and washbowls; anti-staining coatings on glazing and head lamp covers in vehicles such as automobiles, trains and aircraft; water repellent, anti-staining coatings on building exteriors; coatings for preventing oil contamination on kitchen ware; water repellent, anti-staining, anti-sticking coatings in telephone booths; and water and oil repellent, anti-fingerprint coatings on artistic objects; coating for preventing fingerprint on compact disks and DVDs. The agent is also used for improving the flow and dispersion of paint additives, resin modifiers and inorganic fillers and for improving lubricity on tape and film.

EXAMPLE

Examples of the invention are given below by way of illustration and not by way of limitation.

Synthesis Example 1

A 200-ml three-necked flask equipped with a thermometer, reflux condenser and stirrer was charged with 88.6 g of a perfluoropolyether-modified diallyldiamide of formula (I) shown below, 40.5 g of m-xylene hexafluoride and 0.187 g of a toluene solution of chloroplatinic acid/vinyl siloxane complex (containing $4.80 \times 10^{-6}$ mol of elemental Pt), which were heated at 80° C. with stirring. Then 5.9 g of trimethoxysilane was added dropwise to the reaction solution, which was ripened for 3 hours at 85° C. After the disappearance of allyl radicals in the reactant was ascertained by $^1$H-NMR, the solvent and the excess trimethoxysilane were distilled off in vacuum, yielding 93.0 g of a colorless clear liquid. The data of $^1$H-NMR and IR spectroscopy of the compound are shown below.

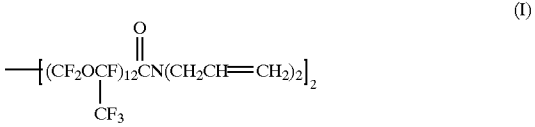

(I)

$^1$H-NMR (TMS standard, ppm)

| —CH$_2$CH$_2$Si≡ | 0.64–0.70 |
| —CH$_2$CH$_2$CH$_2$— | 1.71–1.93 |
| —CONCH$_2$CH$_2$— | 3.28–3.51 |
| —Si(OCH$_3$)$_3$ | 3.47–3.62 |

IR (KBr plate, liquid-membrane method, cm$^{-1}$, see FIG. 1)

2955-2820 (C—H)

1680 (CON)

1310-1090 (C—F)

From the above data, the compound was identified to have the structural formula below.

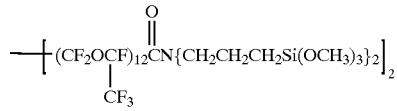

Synthetic Example 2

A compound of the formula shown below was prepared by the same procedure as Synthetic Example 1 except that methyldimethoxysilane was used instead of the trimethoxysilane.

Synthetic Example 3

By following the same procedure as Synthetic Example 1 except that a compound of the formula (II) shown below

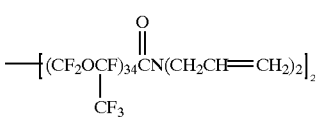

(II)

was used instead of the perfluoropolyether-modified diallyldiamide of formula (I), a compound of the following formula was prepared.

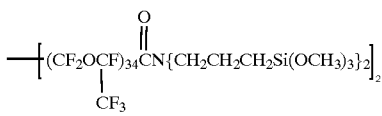

Synthetic Example 4 (Comparison)

By following the same procedure as Synthetic Example 1 except that a compound of the formula (III) shown below

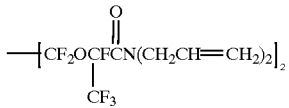

was used instead of the perfluoropolyether-modified diallyl-diamide of formula (I), a compound of the following formula was prepared.

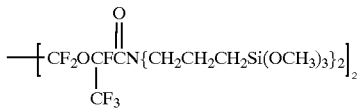

Examples 1-1 to 1-3

In 97.0 g of perfluoro(2-butyltetrahydrofuran) was dissolved 3.0 g of the perfluoropolyether-modified aminosilane synthesized in each of Synthetic Examples 1 to 3. The solution was brush coated onto a glass plate of 2.5×10×0.5 cm, and allowed to stand for one hour in an atmosphere at 25° C. and humidity 70% whereby the coating cured. This test specimen was examined by the following tests.

(1) Water and Oil Repellent Test

Using a contact angle meter model A3 (Kyowa Kaimen Kagaku K. K.), the contact angle of the cured coating with water and n-hexadecane was measured as the rating of water and oil repellency.

(2) Parting Test

A Cellophane adhesive tape strip (25 mm wide) was attached to the surface of the cured coating. Using a tensile tester, the tape strip was pulled and peeled at an angle of 180° and a rate of 300 mm/min. The force required for peeling was measured as the rating of parting property.

(3) Durability Test

The surface of the cured coating was wiped 30 strokes with cellulose non-woven fabric under a predetermined load. Thereafter, the contact angle with water was measured as in test (1), from which durability was evaluated.

(4) Hydrolysis (Film Formation) Test

In 97.0 g of perfluoro(2-butyltetrahydrofuran) was dissolved 3.0 g of the perfluoropolyether-modified aminosilane synthesized in each of Synthetic Examples 1 to 3. The solution was brush coated onto a glass plate of 2.5×10×0.5 cm. The coating was allowed to stand for 10 minutes in an atmosphere at 25° C. and humidity 70% whereupon the uncured residue on the surface was washed away by flowing perfluoro(2-butyltetrahydrofuran). The contact angle of the coated glass surface with water was measured as the rating of hydrolysis or film formability.

The results of these tests (1) to (4) are shown in Table 1.

Comparative Example 1-1

A cured coating was obtained and tested as in Examples 1-1 to 1-3 except that the fluoroaminosilane synthesized in Synthetic Example 4 was used instead of the fluoroaminosilanes in Examples 1-1 to 1-3. The test results are also shown in Table 1.

Comparative Example 1-2

A cured coating was obtained and tested as in Examples 1-1 to 1-3 except that a compound of the following formula (IV) was used instead of the fluoroaminosilanes in Examples 1-1 to 1-3. The test results are also shown in Table 1.

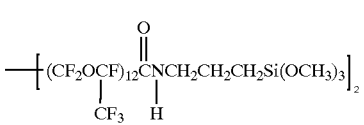

TABLE 1

| | Water and oil repellency (deg) | | Parting | Durability | Hydrolysis |
|---|---|---|---|---|---|
| | Water | n-hexadecane | (g/25 mm) | (deg) | (deg) |
| E 1-1 | 113 | 72 | 19 | 111 | 110 |
| E 1-2 | 115 | 73 | 20 | 113 | 108 |
| E 1-3 | 116 | 73 | 16 | 114 | 112 |
| CE 1-1 | 100 | 62 | 89 | 97 | 96 |
| CE 1-2 | 111 | 71 | 22 | 100 | 82 |

The coatings of Examples show water and oil repellency and parting property at least comparable to the prior art coating (Comparative Example 1-2) and are improved in durability and hydrolysis (or film formation). The coating of Comparative Example 1-1 is inferior in water and oil repellency and parting property to the coatings of Examples and unacceptable on practical use.

It is thus evident that the perfluoropolyether-modified aminosilane of the invention forms a tough coating on a substrate surface and is applicable as a surface treating agent having improved water and oil repellency and parting property.

Examples 2-1 to 2-3

In 495.0 g of perfluoro(2-butyltetrahydrofuran) was dissolved 5.0 g of the perfluoropolyether-modified aminosilane synthesized in each of Synthetic Examples 1 to 3. Trifluoromethanesulfonic acid, 0.05 g, was added to the coating solution, followed by thorough agitation. An acrylic resin plate of 10×10×0.8 cm having a hard coat of silicone resin thereon was dipped in the coating solution. The coating was allowed to stand for 2 hours in an atmosphere at 40° C. and humidity 85% whereby the coating cured. The surface was wiped off with dry fabric, completing the cured coating. This test specimen was examined by the following tests.

(1) Water Repellent Test

Using a contact angle meter model A3 (Kyowa Kaimen Kagaku K. K.), the contact angle of the cured coating with water was measured as the rating of water repellency.

(2) Anti-staining Test

About 30 g of a contaminant shown in Table 2 was cast over the coated acrylic resin plate. It was examined how the contaminant stuck to the coating. The contaminant-applied plate was air dried at room temperature for 15 minutes and then wiped with dry fabric. It was examined how the contaminant was wiped off. Evaluation was made according to the following criterion.

Contaminant sticking
O: little sticking
Δ: some sticking
X: heavy sticking
Contaminant wiping-off
O: light wiping Δ: difficult to wipe off, but no track
X: difficult to wipe off, with track left
The results are shown in Table 2.

Comparative Example 2-1

A coating solution was prepared and examined as in Examples 2-1 to 2-3 except that the fluoroaminosilane synthesized in Synthetic Example 4 was used instead of the inventive aminosilane. The results are also shown in Table 2.

Comparative Example 2-2

A coating solution was prepared and examined as in Examples 2-1 to 2-3 except that $C_8F_{17}CH_2CH_2Si(OCH_3)_3$ was used instead of the inventive aminosilane. The results are also shown in Table 2.

Comparative Example 2-3

Without applying the coating solution, the acrylic resin plate was examined as in Examples 2-1 to 2-3. The results are also shown in Table 2.

TABLE 2

| | Water repellency (deg) | Anti-staining | | | |
| | | Chinese Ink | | Squalane | |
| | | Sticking | Wiping | Sticking | Wiping |
|---|---|---|---|---|---|
| E 2-1 | 112 | ○ | ○ | ○ | ○ |
| E 2-2 | 113 | ○ | Δ | ○ | ○ |
| E 2-3 | 113 | ○ | ○ | ○ | ○ |
| CE 2-1 | 101 | Δ | X | Δ | X |
| CE 2-2 | 102 | Δ | Δ | Δ | Δ |
| CE 2-3 | 73 | Δ | X | X | X |

Examples 3-1 to 3-3

In 495.0 g of perfluorohexane was dissolved 5.0 g of the perfluoropolyether-modified aminosilane synthesized in each of Synthetic Examples 1 to 3. The coating solution was spin coated onto a glass lens. The coating was allowed to stand for 2 hours in an atmosphere at 40° C. and humidity 85% whereby the coating cured. The surface was wiped off with dry fabric, completing the cured coating. This test specimen was examined by the following tests.

(1) Water Repellent Test

Using a contact angle meter model A3 (Kyowa Kaimen Kagaku K. K.), the contact angle of the coated lens with water was measured as the rating of water repellency.

(2) Anti-staining Test

The forefinger was pressed against the coated lens for 5 seconds, leaving a fingerprint. The lens was visually examined whether the fingerprint was definite or obscure. It was also examined how the fingerprint was wiped off with dry fabric. The evaluation was made according to the following criterion. The rating was an average of a 5-member panel.

Fingerprint marking
O: little fingerprint left
Δ: some fingerprint
X: definite fingerprint
Fingerprint wiping-off
O: light wiping
Δ: difficult to wipe off, but no track
X: difficult to wipe off, with track left
The results are shown in Table 3.

Comparative Example 3-1

A coating solution was prepared and examined as in Examples 3-1 to 3-3 except that the fluoroaminosilane synthesized in Synthetic Example 4 was used instead of the inventive aminosilane. The results are also shown in Table 3.

Comparative Example 3-2

A coating solution was prepared and examined as in Examples 3-1 to 3-3 except that $C_8F_{17}CH_2CH_2Si(OCH_3)_3$ was used instead of the inventive aminosilane. The results are also shown in Table 3.

Comparative Example 3-3

Without applying the coating solution, the glass lens was examined as in Examples 3-1 to 3-3. The results are also shown in Table 3.

TABLE 3

| | Water repellency (deg) | Fingerprint sticking | Fingerprint wiping-off |
|---|---|---|---|
| E 3-1 | 113 | ○ | ○ |
| E 3-2 | 115 | ○ | ○ |
| E 3-3 | 116 | ○ | ○ |
| CE 3-1 | 100 | Δ | Δ |
| CE 3-2 | 108 | Δ | X |
| CE 3-3 | 34 | X | X |

It is evident that the modified aminosilanes of the invention are advantageously used in a wide variety of coating applications to form cured coatings having improved water and oil repellency and anti-staining property.

Japanese Patent Application No. 2000-314657 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claim is:

1. A perfluoropolyether-modified aminosilane having the formula (1):

$$\left[ (C_xF_{2x}O)_mC_yF_{2y}C(=O)-N \begin{pmatrix} Q^1-SiX^1_n R^1_{3-n} \\ Q^2-SiX^2_n R^2_{3-n} \end{pmatrix} \right]_2 \tag{1}$$

wherein $X^1$ and $X^2$ each are a hydrolyzable radical, $R^1$ and $R^2$ each are a lower alkyl radical or phenyl radical, $Q^1$ and $Q^2$ each are a divalent organic radical, m is an integer of 2 to 50, n is 2 or 3, x is an integer of 1 to 4, and y is an integer of 0 to 4.

2. The perfluoropolyether-modified aminosilane of claim 1 wherein the perfluoropolyether portion represented by $(C_xF_{2x}O)_m$ is represented by the formula:

$$-(CF_2OCF)_{\overline{m}}-$$
$$\quad\quad\ |$$
$$\quad\quad CF_3$$

wherein m is as defined above.

3. The perfluoropolyether-modified aminosilane of claim 1 wherein the hydrolyzable radical X is an alkoxy radical.

4. The perfluoropolyether-modified aminosilane of claim 1 wherein $Q^1$ and $Q^2$ each are $CH_2CH_2CH_2$.

5. A surface treating agent primarily comprising the perfluoropolyether-modified aminosilane of the formula (1):

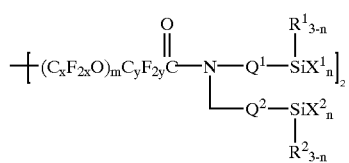

(1)

wherein $X^1$ and $X^2$ each are a hydrolyzable radical, $R^1$ and $R^2$ each are a lower alkyl radical or phenyl radical, $Q^1$ and $Q^2$ each are a divalent organic radical, m is an integer of 2 to 50, n is 2 or 3, x is an integer of 1 to 4, and y is an integer of 0 to 4 or a partial hydrolytic condensate thereof or both.

6. An article having on its surface a cured coating primarily comprising the perfluoropolyether-modified aminosilane of the formula (1):

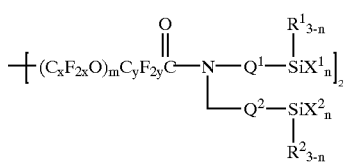

(1)

wherein $X^1$ and $X^2$ each are a hydrolyzable radical, $R^1$ and $R^2$ each are a lower alkyl radical or phenyl radical, $Q^1$ and $Q^2$ each are a divalent organic radical, m is an integer of 2 to 50, n is 2 or 3, x is an integer of 1 to 4, and y is an integer of 0 to 4 or a partial hydrolytic condensate thereof or both.

* * * * *